United States Patent [19]

Cameron et al.

[11] Patent Number: 4,993,948

[45] Date of Patent: Feb. 19, 1991

[54] APPLICATOR FOR DENTAL MATERIAL

[76] Inventors: Frederick J. Cameron, 59 Maywood Dr., San Rafael, Calif. 94901; Carl L. Cranke, 31403 NE. 152nd Ave., Battleground, Wash. 98604

[21] Appl. No.: 428,966

[22] Filed: Oct. 30, 1989

[51] Int. Cl.⁵ .............................................. A61C 5/04
[52] U.S. Cl. .................................... 433/90; 222/387; 604/236; 604/311
[58] Field of Search ............... 433/90, 89; 222/387; 604/121, 236, 311, 32, 33, 38, 218, 222

[56] References Cited

U.S. PATENT DOCUMENTS

| | | | |
|---|---|---|---|
| 3,293,749 | 12/1966 | George et al. | 433/90 |
| 3,417,971 | 12/1968 | Blank et al. | 433/90 |
| 3,747,812 | 7/1973 | Karman et al. | 222/387 |
| 3,757,981 | 9/1973 | Harris, Sr. et al. | 604/236 |
| 4,159,570 | 7/1979 | Baskas et al. | 433/90 |

FOREIGN PATENT DOCUMENTS 32826  7/1981 European Pat. Off. ............ 604/121

Primary Examiner—Cary E. Stone
Attorney, Agent, or Firm—Lothrop & West

[57] ABSTRACT

For free-hand use by a dentist, there is provided a cylinder containing tooth filling material urged out of the cylinder by spring pressure, sometimes augmented by thumb pressure against the end of a piston rod in the cylinder. Flow of the material out of the cylinder through a removable and replaceable flexible curved nozzle is under control of a valve located to be readily manipulated between open and closed positions by the same hand of the dentist. Preferably the filling material is in a discrete capsule containing enough filling material for several teeth and easily placed in and removed from the cylinder.

5 Claims, 2 Drawing Sheets

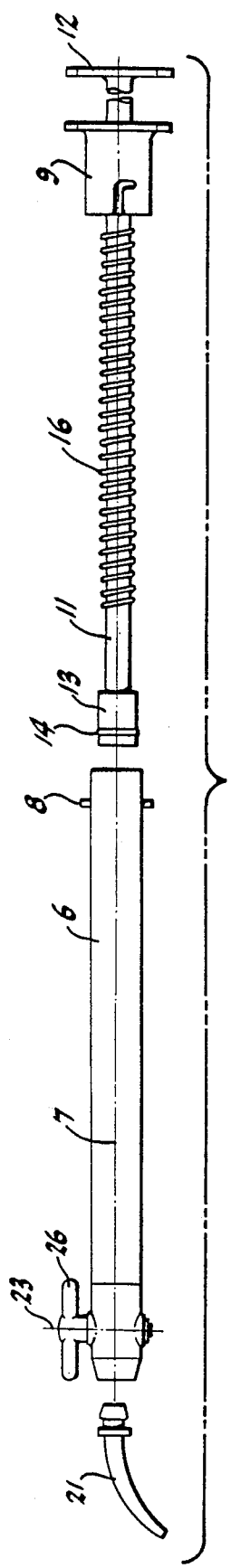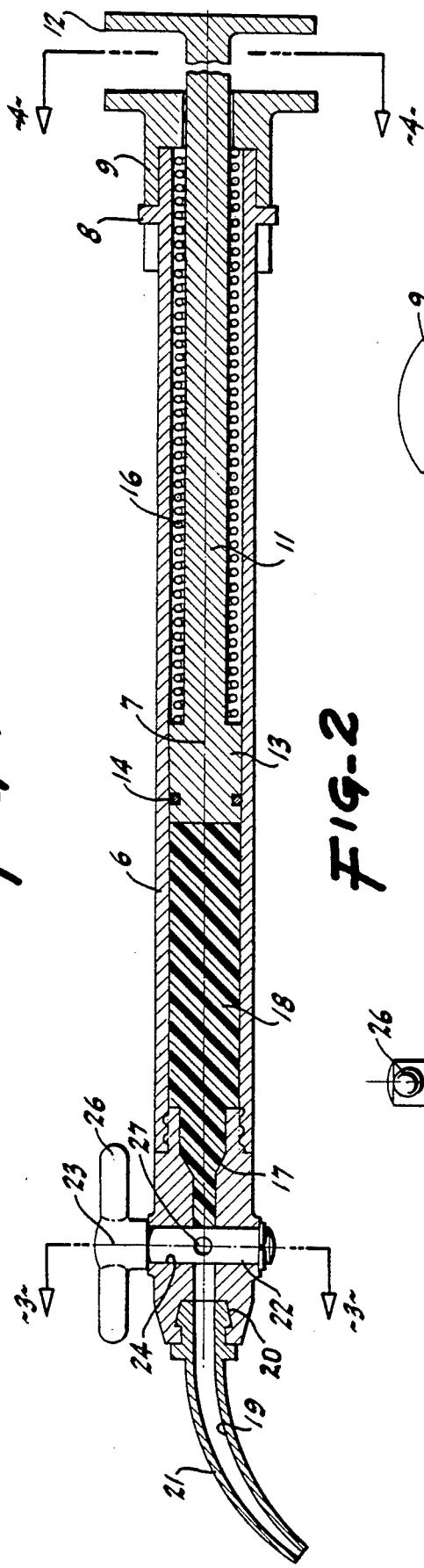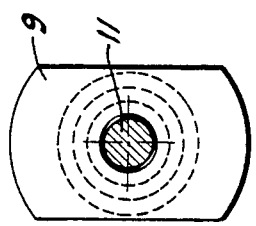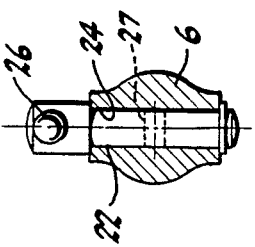

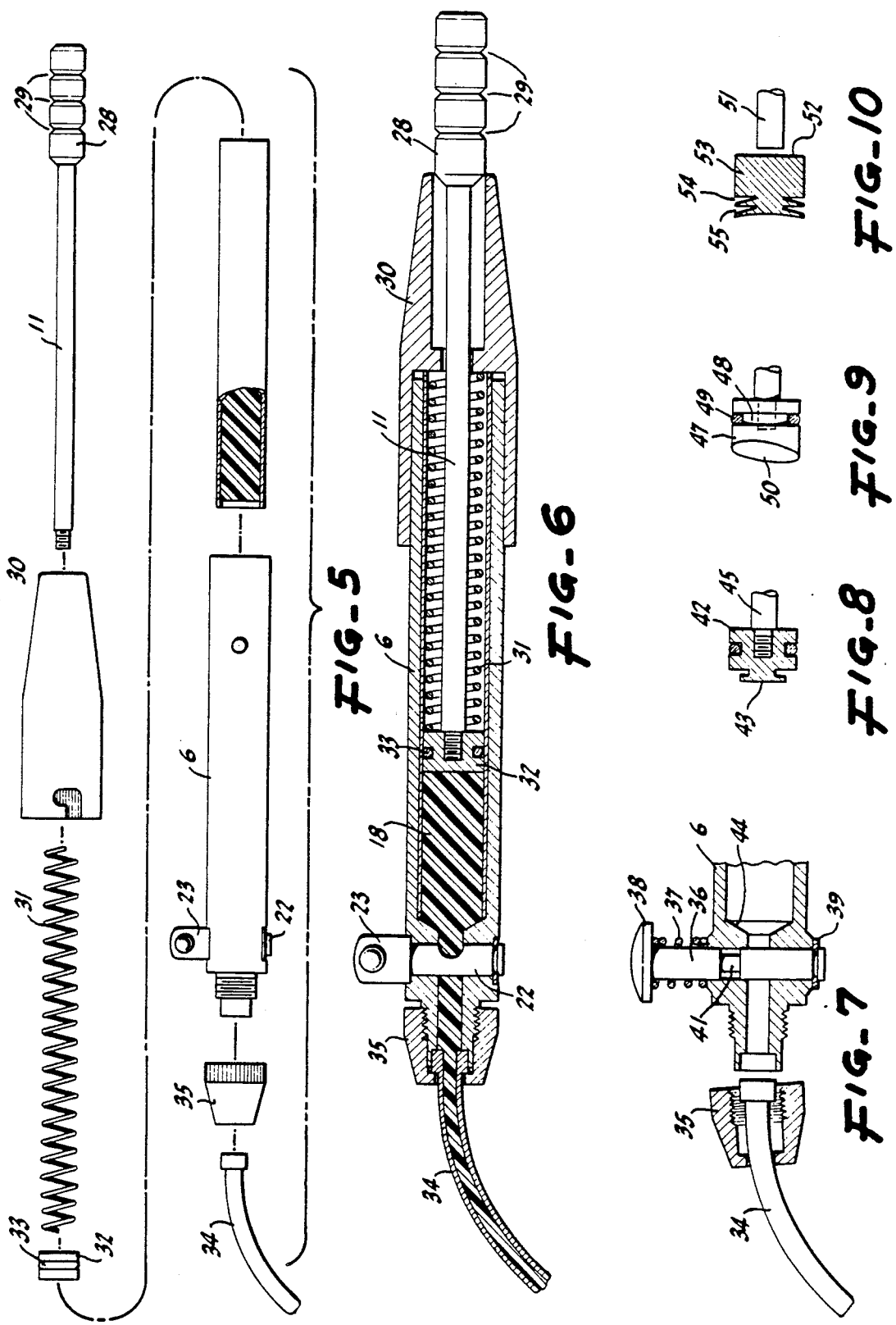

APPLICATOR FOR DENTAL MATERIAL

BACKGROUND OF THE INVENTION

1. Field of the Invention

The applicator is especially for use by dentists in deriving a pattern for tooth inlays and crowns and for temporarily positioning an initially flowable, ultimately hardenable material in a tooth cavity.

2. Description of the Related Art

A search by the applicants has developed the following U.S. Pat. Nos.:

| | | |
|---|---|---|
| 2,098,658 | Goltman et al. | November 9, 1937 |
| 3,521,356 | Newman | July 21, 1970 |
| 3,593,423 | Jones et al. | July 20, 1971 |
| 3,605,745 | Hodosh | September 20, 1971 |
| 3,641,673 | Jochems | February 15, 1972 |
| 3,827,147 | Condon | August 6, 1974 |
| 3,854,209 | Franklin et al. | December 17, 1974 |
| 3,968,796 | Baker | July 13, 1976 |
| 4,306,863 | Law et al. | December 22, 1981 |
| 4,330,280 | Dougherty et al. | May 18, 1982 |
| 4,693,684 | Blatherwick et al. | September 15, 1987 |
| 4,708,650 | Holewinski et al. | November 24, 1987 |
| 4,768,955 | Hirdes | September 6, 1988 |

Each disclosure, above, has one or more major differences from the claimed disclosure herein.

SUMMARY OF THE INVENTION

A manually operable, balanced valve is in the outlet nozzle on a cylindrical applicator body for dental material. There are outside grips for manual rotation or axial translation of the valve to block or to permit outflow of the dental material from the nozzle.

BRIEF DESCRIPTION OF THE DRAWINGS

FIG. 1 is a side elevation of one form of the device, the parts being shown in exploded positions.

FIG. 2 is a cross-section to a larger scale on a longitudinal, transverse, axial plane through the device of FIG. 1 in assembled, working condition.

FIG. 3 is a transverse cross-section of the device of FIG. 1, the plane of section being indicated by the line 3—3 of FIG. 2.

FIG. 4 is an end elevation of the device of FIG. 1, the plane of view being indicated by the line 4—4 of FIG. 2.

FIG. 5 is an exploded or displaced view mostly in side elevation but with a part in cross-section, showing a loaded or operable applicator according to the invention.

FIG. 6 is a cross-sectional view on a longitudinal, diametrical plane, except for portions in side elevation of the applicator of the invention.

FIG. 7 is, for the most part, a cross-section on a longitudinal diametrical plane of a modified form of valve arrangement and adjacent parts of a structure otherwise like FIG. 6, some of the parts being in disconnected or exploded positions and with some parts in side elevation.

FIG. 8 is a cross-section on a longitudinal, diametrical plane of a modified form of plunger piston, and part of an associated rod in side elevation.

FIG. 9 is a side elevation of a different form of plunger piston and associated piston rod with an O-ring seal on the piston, shown in cross-section on a longitudinal, diametrical plane.

FIG. 10 is, in part, a cross-section on a longitudinal, diametrical plane of a modified form of piston plunger and also a side elevation of a piston or plunger rod co-acting with the piston plunger.

DESCRIPTION OF THE PREFERRED EMBODIMENTS

In various dental situations, it is necessary to provide a cavity filling material. Currently, filling materials of semi-plastic, semi-fluid substances are often utilized. These have the property of hardening in place shortly after they have been appropriately positioned and contoured and exposed to the air. Often such materials are readily available in semi-solid, cylindrical capsule form or in other discrete bodies of initially readily maneuverable and manageable sizes and shapes.

To accommodate and employ such materials, we preferably provide, in one embodiment, a circular-cylindrical body 6 or housing having a central axis 7. At one end, the operator's end, the body 6 is open and is provided with an external fastening 8 such as a bayonet pin or a thread interengageable with a complementarily contoured end cap 9. The end cap serves as a bearing for a slidable actuating rod 11. At its outermost, operator's end the rod 11 has a pressure plate 12 or thumb stop. At its other end, the rod 11 has a piston 13. If desired, the piston is provided with a sealing O-ring 14. The piston is abutted by one end of a spring 16, contained in the tubular body 6, the other end of the spring abutting the cap 9. Against the piston 13 as well as the interior end plug 17 screwed into the end of the enclosure 6 is an individual or separate, discrete mass 18 of filling material. The material is appropriate for positioning in the tooth cavity and can initially be a separate, unbounded mass or can be in the form of a defined capsule. The material 18 is sufficiently fluid to be readily discharged through an outlet opening 19 through the end wall or plug 17 of the device. The opening 19 continues through a nozzle 21 of sufficient size and of appropriate direction for easy and ready maneuverability into any desired position to confront the particular cavity being treated. The nozzle 21 is preferably molded of a yieldable or flexible plastic sufficiently deformable as to be readily snapped into and withdrawn from its receptor socket 20 at the end of the end plug 17. Different nozzles may easily be used for different patients and are economical enough to be discarded after each patient.

To control flow through the passage 19 and from the nozzle 21 there is provided a rotary valve 22. This is an even, cylindrical body symmetrical about a cross axis 23 and extends from both ends of a cross bore 24 in the nozzle. So that the balanced rotary or plug valve 22 can be appropriately rotated, there is fitted an exterior, manually engageable cross rod 26. In one plug rotary position, a bore 27 through the plug valve is placed in alignment with the passage 19. In a position substantially or approximately at right angles thereto, the bore 27 is out of registry with the passage 19 and interrupts or prevents outflow of the plastic material from the capsule 18. The rotated position of the cross rod 26 helps regulate the amount or rate of discharge of the filling material.

In the use of the first form of this device, the end cap 9 is removed along with the spring 16 and the plunger 13, so as to leave the interior of the cylinder 6 entirely empty. A capsule 18 or charge of appropriate size, shape and composition of semi-fluid or semi-viscous material is installed. The capsule is preferred, as it is self-contained and individually manipulable. The charge or capsule is dropped into position substantially against the end wall 17. The plug valve 22 remains closed. The plunger 13 and spring 16 are reintroduced into the cylinder. The cap 9 is then reinstalled, simultaneously compressing and holding the spring 16 in a compressed state. The initial effect of the spring force is slightly to displace the piston and some of the material of the charge or capsule up to the surface of the closed valve 22.

When the dentist is ready to utilize the charged device, he simply turns the cross rod 26 through about a quarter turn. He can hold the body 6 and turn the cross rod 26 with one hand. Valve opening aligns the passage 27 with the passage 19 and makes a flow path for the plastic material to advance into and to discharge from the nozzle 21. The dentist can manipulate the structure very easily and simply because he is not required to furnish manual force to eject material from the cylinder to the tooth area. The spring furnishes the ejection force. All the dentist has to do is to guide or position the nozzle 21 by lightly holding the body 6 in position. He can facilely maneuver the barrel or body 6 into whatever attitude he desires. The spring 16 continues to expel the material until the dentist is finished. Thereupon, he again moves the cross rod 26 and rotates the balanced valve 22 into its shutoff position, thus interrupting the discharge of the plastic material.

While normally the pressure plate 12 need not be contacted during discharge of the plastic material, thumb pressure on the plate 12 can readily augment the spring force. The plate 12 also helps to recompress or recock the spring 16 just before the user reattaches the collar 9 with the bayonet or threaded connection to a refilled cylinder 6 or barrel.

The amount of material in the capsule 18 can be more than is necessary for use with a single cavity. The dentist, by opening and closing the valve 22 from time to time, can release and position different regulated amounts of the plastic material in different locations in the patient's teeth. The device can easily be sterilized between uses on a succession of patients. When the capsule 18 is substantially or fully used, any remaining portion of filling material can be expelled to waste by pressure upon the plate 12. This causes the rod 11 and piston 13 to eject forcibly any remains of the material. The structure can then be completely disassembled, sterilized, recharged, reassembled and reused.

In the embodiment of the invention shown in FIGS. 5-10, the general arrangement, purpose and operation are like those just described. There are some changes. The rod 11 at one end has an enlarged stem 28 with a number of turned grooves 29 affording a visible and tactile indication of the axial position of the rod within the surrounding tubular end 30. Each groove represents one charge of repair material. The spring 31 is somewhat stronger than before so that the end cap 9 and the pressure plate 12 can be dispensed with. The inner end of the rod 11 is threaded and couples to a piston 32 carrying an O-ring seal 33. A charge 18 of material is in the cylinder 6 or body as before and, in the version of FIG. 6, is controlled by a balanced turn or plug valve 22, as before. The discharge from an open valve 22 is through the end of the body 6 and into a changeable and flexible plastic nozzle 34 held in position by a threaded collar 35.

A variation, shown in FIG. 7, is not a rotary discharge valve, but a transversely movable valve 36 ordinarily urged to its closed position by a spring 37 interposed between the body 6 and a thumb cap 38. Travel of the valve 36 is limited by a cut or split washer 39 in a groove in the lower end of the valve. When a cap 38 is depressed by the operator, against the urgency of the spring 37, the valve 22 is moved so that a reduced portion 41 aligns with the passages to allow flow of filling material into and through the nozzle 34.

In FIG. 8 is another variation in that a piston 42, generally like the piston 32 as shown in FIG. 6, is screwed onto a rod 45 and has a forward, circular knob 43 for engagement by the user's fingers and fingernails or by a tool whenever the piston 42 and the rod 45 are relatively rotated. The forward circular edge of the knob 43 is relatively sharp and when in abutment with the conical inside wall 44 of the cylinder 6 makes a tight closure.

In FIG. 9, the piston 47 is about as before and has a groove 48 containing an O-ring 49. It also has a bevelled or offset front planar face 50. When advancing and acting against the filling material, this offset face 50 imparts a transverse component to the filling material and tends to displace any air bubbles and to afford good final mixing.

In FIG. 10, there are two main variations. First, the rod 51 is not threaded and merely abuts the adjacent, flat face 52 of the piston 53. This is a more economical construction for devices that are used but once and then discarded. The second difference in the FIG. 10 structure is that sealing of the plunger 53 in the cylinder is not accomplished by O-rings. Rather, the piston itself has several; here, two, grooves 54 and 55 extending circumferentially and of sufficient flexibility to engage the cylinder wall and themselves form a yieldable, effective seal.

What is claimed is:

1. An applicator for dental material comprising:
   a. a cylindrical body adapted to receive a semi-fluid charge;
   b. a nozzle on one end of said cylindrical body and communicating therewith;
   c. a piston plunger reciprocable in said cylindrical body for displacing said charge from said cylindrical body to flow through said nozzle;
   d. a spring;
   e. means for mounting said spring in said body for engagement with said piston plunger;
   f. a removable cap mounted on the other end of said body and engageable with said spring for holding said spring in an initially compressed state to displace said piston plunger toward said nozzle;
   g. a flow controlling valve in said body between said piston plunger and said nozzle and movable between one position allowing said flow and another position blocking said flow; and,
   h. means connected to said valve and disposed outside said nozzle in position to be operated by a person holding said cylindrical body for moving said valve between said one position and said other position.

2. A device as in claim 1 in which said valve is a rotary plug valve.

3. A device as in claim 1 in which said cylindrical body has a body axis and said valve includes a plug shiftable between an open position and a closed position by the same hand of a person holding said cylindrical body at a location axially adjacent to said valve and separated from said nozzle by said valve.

4. A device as in claim 1 in which means defining indicia are on one end of said piston plunger and adjacent the end of said cylindrical body to indicate the relative position of said piston plunger and said cylindrical body.

5. A device as in claim 1 in which the direction of movement of said valve is substantially at right angles to the direction of material flow, and said valve includes a reduced portion aligned with the flow in said one position and removed from the flow in said other position.

* * * * *